United States Patent [19]

Fischler et al.

[11] Patent Number: 4,527,567
[45] Date of Patent: Jul. 9, 1985

[54] METHOD AND APPARATUS FOR AUTOMATICALLY EVALUATING THE QUALITY OF THE PERFORMANCE OF A CARDIAC PACING SYSTEM

[75] Inventors: Henryk Fischler; Yaakov Krupka, both of Rehovot; Salamon Behar, Tel Aviv, all of Israel

[73] Assignee: Yeda Research & Development Company, Ltd., Rehovot, Israel

[21] Appl. No.: 401,543

[22] Filed: Jul. 26, 1982

Related U.S. Application Data

[63] Continuation-in-part of Ser. No. 136,300, Apr. 1, 1980, abandoned, which is a continuation-in-part of Ser. No. 939,777, Sep. 5, 1978, abandoned, which is a continuation of Ser. No. 752,548, Dec. 20, 1976, abandoned.

[51] Int. Cl.³ .............................................. A61N 5/04
[52] U.S. Cl. .............................. 128/419 PT; 128/697
[58] Field of Search .................. 128/696, 697, 419 PT, 128/702–704, 708, 902

[56] References Cited

U.S. PATENT DOCUMENTS

| | | | |
|---|---|---|---|
| 3,534,282 | 10/1970 | Day | 128/902 |
| 3,552,386 | 1/1971 | Horth | 128/703 |
| 3,780,727 | 12/1973 | King | 128/697 |
| 3,782,367 | 1/1974 | Hochberg et al. | 128/697 |
| 3,885,552 | 5/1975 | Kennedy | 128/419 PT |
| 3,901,247 | 8/1975 | Walmsley | 128/419 PT |
| 3,903,874 | 9/1975 | Shakespeare | 128/696 |
| 3,939,824 | 2/1976 | Arneson et al. | 128/708 |
| 3,940,692 | 2/1976 | Neilson | 128/702 |
| 4,115,864 | 9/1978 | Vick et al. | 128/703 |

Primary Examiner—William E. Kamm
Attorney, Agent, or Firm—Browdy and Neimark

[57] ABSTRACT

An extra-corporeal, self-contained, on-line, beat-to-beat pacemaker function analyzer (PFA) for automatic evaluation and indication of the quality of performance of cardiac pacing systems implanted in place for: routine examination of ambulatory patients; long-term surveillance of hospitalized patients; and examination of ECG traces (including pacing artefacts) of remote pacemaker patients, transferred by telephone or radio to a central follow-up station. The PFA provides a comprehensive examination of asynchronous, demand and demand-hysteresis pacemakers of all makes, including the state of the pacemaker's battery, the intactness of the electronic circuitry and of the electrodes, and the proper location of the electrodes in the heart.

22 Claims, 7 Drawing Figures

METHOD AND APPARATUS FOR AUTOMATICALLY EVALUATING THE QUALITY OF THE PERFORMANCE OF A CARDIAC PACING SYSTEM

REFERENCES TO RELATED APPLICATIONS

The present patent application is a continuation in part of U.S. patent application Ser. No. 136,300 filed on Apr. 1, 1980, now abandoned which in turn, was a continuation in part of U.S. application Ser. No. 939,777 filed on Sept. 5, 1978, now abandoned, which in turn, was a continuation of U.S. application Ser. No. 752,548 filed on Dec. 20, 1976, now abandoned, all incorporated herein by reference as if here set forth in full.

FIELD OF THE INVENTION

Pacemaker Function Analyzer—a device for automatic evaluation and indication of the functioning of cardiac pacing systems.

BACKGROUND OF THE INVENTION

The number of cardiac patients dependent on artificial pacing to keep their heart rate at a normal level has been growing rapidly since implantable pacemakers became commercially available. Presently, in the developed countries about a hundred to three hundred patients per one million population join the group of pacemaker wearers each year with an average life expectancy of five years. Thus the number of pacemaker patients may grow in a few years to an absolute value of about 1,250 per one million population (or 275,000 patients in the U.S.A.). The health institutions will be required to provide proper medical care for all of the patients by regular checking of the implanted apparatus.

Special pacemakers clinics have already been established, mostly at the cardiological departments dealing with pacemaker implantations. A common procedure is for the patient to visit the clinic once every three months in the first year after implantation, to keep track of the actual state of the pacing system. Then, as the anticipated lifetime of the pacemaker elapses due to battery exhaustion, the pacemaker function is tested once a month and even more often in order to determine the exact time for its replacement. Presently the most common failure of the pacemakers is exhaustion of the supply battery. However, attentions must also be paid to possible functional defects arising from failing electrical devices and components, from short circuits due to defective technological processes during manufacture, and also to disturbances in delivery of the pacing stimuli and/or in sensing the heart activity due to electrode displacement or breakage.

Special methods have been elaborated for pacemaker evaluation which require sophisticated instrumentation and systems, and professional personnel in cardiology for supervision, carrying out the tests and interpretation of the obtained results. At the present time, the pacemaker check-up arrangements constitute a serious burden for the cardiologists and patients, and their impact will grow steadily with the rise in number of pacemaker patients. The cardiologist has to spend much time on auxiliary routine work, while the patient and his family are burdened both with wasted time and the expenses involved in special visits and travel to pacemaker clinics sometimes located far from home.

In the last few years a trend may be distinguished in the development of pacemaker testing instrumentation: the partial substitution of sophisticated check-up systems by simple, self-contained apparatus. The objective is to allow more frequent pacemaker evaluation in the vicinity of the patient's home or at the home itself. A number of new instrumentation models have already been announced for marketing. However, in principle, they test only one function of the pacemaker, namely the state of the supply battery by counting the pacing rate or by measuring the duraction (width) of the pacing artefact.

DISCUSSION OF THE PRIOR ART

D. L. Bowers, U.S. Pat. No. 3,426,748; Feb. 11, 1969, concerns a pacing threshold analyzer located outside the body, which is capable of control by induction the amount of energy delivered from an electronic stimulator implanted in the body to a body organ. Thus, it allows assessing the minimum energy that is necessary to stimulate a particular organ. All this, provided the internal stimulator includes a coil such as L100 in FIG. 3a or L200 in FIG. 3b, in which the induced signal affects the operating point of the stimulus generating stage. There is no mention as to the method of recognition or indications of organ (heart) "capture" by the pacing stimulus.

H. M. Hochberg, U.S. Pat. No. 3,782,367; Jan. 1, 1974, concerns a technique and a monitoring system capable of automatic evaluation of the effectiveness of cardiac pacing (heart "capture") in a variety of pacing modes, and of alarming in cases of non-capture due to a pacemaker failure. For this purpose certain logic operations are undertaken on the timing sequences of pulses designating the occurrence of the QRS complexes and the pacing artifacts. The general idea of checking the effectiveness of pacing is similar to that in our disclosure. The difference is in the method and the criterions used by us for detection and recognition of the QRS-complexes and of the pacing artefacts, and for judging the heart "capture". To our knowledge, our methods and criterions cover a broader variety of electrocardiogram events taking place in pacemaker patients (QRS in the "separated" and "fused" forms, see text in the following of this disclosure), and provide more stringent and reliable algorithms for their recognition, and for performing the heart "capture" test. The high reliability of our testing procedure has been confirmed by the results of multiple patient examinations (on 198 patents): false negative QRS recognition—0.29%, false negative pacing artefact recognition—0.21%, no (zero) false positive recognition, no (zero) false heart "capture" judgment.

J. R. Kennedy, U.S. Pat. No. 3,885,552; May 27, 1975, concerns a method and system for the detection and transmission of ECG data including pacing artefacts, through a telephone link from a remote location to a central clinic. The stress is laid here essentially on use of the information contained in a pacing pulse for the sake of analysis of the state of the pacer's battery, and on providing means for undisturbed transmission of information together with the ECG signals through a telephone link.

In our invention, we utilize the same (well known) pacemaker features of a varying pacing rate (decrease) and pacing pulse width (increase) with the depletion of the supply battery for evaluation of the state of this battery. The difference in comparison to the Kennedy patent is in the methods and criteria used by us for detection and recognition of the QRS-complexes and of the pacing artefacts, and in the logic procedures and circuitry implemented for judging the possible kinds of the pacer's malfunction. This provides the high reliability of our testing procedures (see: remarks to the Hochberg patent) and the possibility of discrimination between the observed malfunctions in pacing rate. Also, in the Kennedy patent only the evaluation of the battery state is made automatically, while the ECG of a patient transmitted to the central clinic must be examined by a cardiac specialist. In our disclosure, the information which comprises all aspects of functioning of the pacing system is handled automatically and the results are automatically displayed.

P. P. Gombrich, U.S. Pat. No. 3,920,005; Nov. 18, 1975, concerns a system for evaluation of a cardiac pacemaker operating in the asynchronous mode, by counting the rate of the pacing pulses and of the cardiac responses (QRS) during a predetermined period of time, presented in conceptual form. While evaluation of the status of the pacer's battery can be based on the pacing pulse rate, an erroneous result might be obtained by judging the heart capture from the identity between the QRS and pacing pulse rates. In case of demand operation, the system is capable of checking whether the patient is pacemaker dependent only. In our disclosure, different methods and criterions are used for decoding and recognition of the QRS and of the pacing artefacts with high reliability (see: Remarks to the Hochberg patent), and the logic procedure to evaluate the pacing function is based on a beat-to-beat analysis of the pacemaker and heart action. Both asynchronous and demand modes are covered fully by the analysis.

W. J. Raddi et al., U.S. Pat. No. 3,769,965; Nov. 6, 1973, concerns a monitor apparatus for picking-up pacing artefacts and transducing them into tone burst for transmission through a telephone link, and a remote receiver for detecting the appearance of the pacing artefacts and measuring the time intervals between them. Knowing the pacing pulse rate, allows evaluation of the state of the pacer's battery; this is the only parameter checked by the monitor. In our disclosure, sophisticated method and criterions are provided to identify the pacing artefacts with high reliability (see: remarks to the Hochberg patent) and to evaluate the pacemaker function on a beat-to-beat basis. Also, all other parameters of the pacemaker action are examined.

T. J. Stern, U.S. Pat. No. 3,742,938; July 3, 1973, concerns a method and system for remote diagnosis of pacemaker patients by picking-up the blood pulses and the pacing artefacts, and transmitting them through a telephone link, presented in a conceptual form. Using the blood pulses in a finger as determinant factors of the heart response to pacing, presents a drawback for time sequence diagnosis, as the time intervals may vary in broad limits between the individual patients. The inventor himself claims (Claim 2) the necessity of establishing standard time intervals for individual patients, which precludes automatization of the testing procedure. In our disclosure, we use QRS monitoring, which are closely time related to the appearance of pacing pulses.

SUMMARY OF THE INVENTION

The present invention, hereinafter called "PFA", relates to an automatic, extra-corporal, self-contained, on-line, beat-to-beat, simply operated pacemaker function analyzer which:

1. Evaluates by its measuring program the following possible failures of asynchronous (fixed rate), demand, and demand-hysteresis pacemakers:
   (a) exhaustion of the supply battery;
   (b) unacceptable changes in the pacing rate due to changes or complete or partial damage of circuitry devices and components or due to defective technological processes.
   (c) impaired pacing due to component or electrode damage;
   (d) ineffective pacing due to improper location or displacement of the electrodes, increase of the pacing threshold, or decrease of the battery voltage;
   (e) impaired sensing of the heart activity by a demand pacemaker and as a result erroneous (in time) pacing, due to improper location or displacement of the electrodes, or due to disorders in the electronic circuitry.

2. In the case of demand pacing the PFA performs the testing under varying conditions of heart activity (natural heart rhythm with intermittent pacing or complete block), without resorting to the methods of forcing unnatural changes of the pacing rate of the pacemaker or of the heart rate.

In the case of continuous overriding of the demand pacemaker by the spontaneous heart rhythm above the permitted slow-rate pacing limit, the spontaneous, normal action of the heart becomes confirmed. However, to exclude malfunction of high rate pacing and to determine the pacing effectivity of the pacer (heart "capture") repeating the test may be recommended until at least two paced beat-to-beat sequences are included within the testing interval. Otherwise, to eliminate the possibility of overlooking a pacemaker failure, there is no choice but to revert it to its fixed rate operation mode (if this option is included in the pacer model), or to artificially slow down the heart rate of the patient. Professional medical supervision is then advisable.

3. The PFA provides discrimination between "normal" and "faulty" operation of the pacemaker and determines the origin of a pacemaker disability. The detailed analysis includes the following outlines:
   For the asynchronous pacemaker:
   (a) Normal-rate effective pacing (normal pacing);
   (b) Normal-rate effective pacing and rhythm competition;
   (c) Normal-rate ineffective pacing;
   (d) Slow-rate pacing;
   (e) Slow-rate ineffective pacing;
   (f) High-rate pacing;
   (g) High-rate ineffective pacing;
   (h) Impaired pacing.
   For the demand pacemaker;
   (a) Spontaneous heart rhythm;
   (b) Normal-rate effective pacing and normal sensing (normal pacing);
   (c) Normal-rate ineffective pacing;
   (d) Slow-rate pacing;
   (e) Slow-rate ineffective pacing;
   (f) High-rate pacing;
   (g) High-rate ineffective pacing;
   (h) Impaired pacing;
   (i) Impaired sensing;
   (j) Impaired sensing and ineffective pacing 4. The PFA provides full patient security by not disturbing the pacemaker action. It is also totally isolated from external high power electric sources (power lines).

5. The PFA automatizes and simplifies the testing procedure and displays automatically the test results. The competence of the patient examination is controlled by sophisticated fail-safe means.
6. In view of the features presented above, the PFA allows carrying out the pacemaker testing under the supervision of medical professionals, not necessarily specialists in pacing, and eventually by paramedical personnel. When operated to give general outcomes: "normal" or "faulty" pacemaker operation, rather than details of pacemaker analysis, the PFA is suited to serve as an aid for periodic testing and for screening out pacemaker patients who need professional cardiological care, in a general medical clinic or at home. Thus, only patients with suspected pacemaker failure will come to the pacemaker clinic, lessening the burden of all the routine examinations.
7. The PFA, when operated to give detailed results of pacemaker analysis and provided with an interfere for interconnection to an ECG recorder and/or memory arrangement for storage of ECGs during the test interval, becomes suited for use in professional pacemaker clinics, as a diagnostic aid to the generally used visual evaluation of the ECG. The recorder ECG data can serve for confirmation of the test findings and for documentation purposes. Automatic discrimination of the pacemaker failure (with the logic processor adapted to resolve a single irregularity) facilitates the diagnosis of the patient, especially in cases of intermittent, single and/or slight deviations from the normal pacemaker function. The PFA presents a convenient substitute for the presently used sophisicated, expensive instruments. It can be easily operated by the medical staff, without need of technical assistance. Also, an out-of-clinic patient can be tested by the pacemaker clinic by transmission of his ECG data through a telephone link. Eventually, the PFA can be integrated within an automatic round the clock diagnostic and answer system.
8. The PFA interfaced with a general purpose coronary care system can be utilized for automatic, long-term, surveillance of hospitalized pacemaker patients.

BRIEF DESCRIPTION OF THE INVENTION

The PFA operates on the following principles:
(a) Continuous sensing and processing of the electrical potentials appearing on the body surface of the patient during pacemaker action and directly related to it (ECG and pacing artefacts);
(b) Recognizing (decoding) the QRS-complexes (R-waves) which signify the contraction of ventricles (heart beats) and the pacing artefacts (Spikes) which result from the pacing pulse, and extracting them from the overall electrical activity including other heart activity, muscle potentials, noise and external interference signals;
(c) Marking the appearance of the QRS-complexes and the pacing artefacts by pulse signals defined in time and duration, which become the determinant signs of the heart and of the pacemaker action; and
(d) Logic processing of the determinant pulses to evaluate the interrelation between the heart and the pacemaker action and vice versa, and thus the correctness of the pacemaker function.

BRIEF DESCRIPTION OF THE DRAWINGS

The invention is illustrated with reference to the enclosed block diagrams and drawings in which.

DETAILED DESCRIPTION OF THE INVENTION

Figure 1:
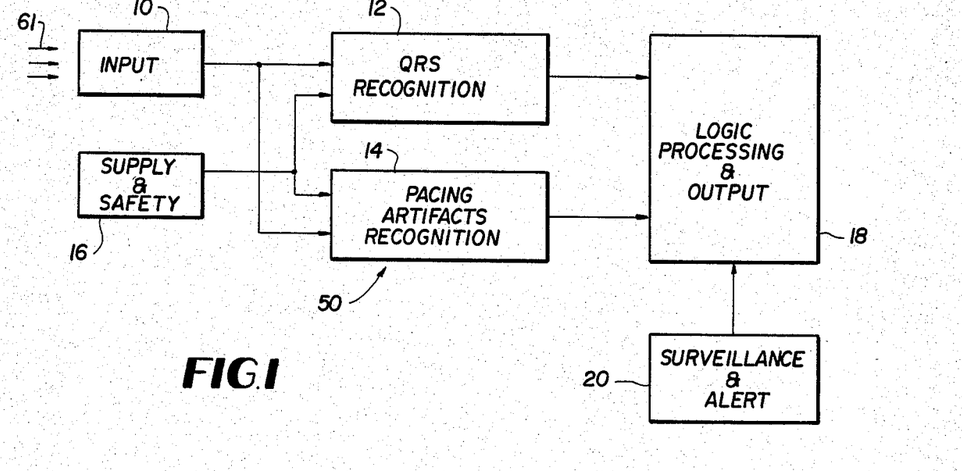
FIG. 1: is an overall block diagram of the invention analyzer.

Referring to FIG. 1, the overall logic of the invention and its manner of organization is shown in the greatly simplified block diagram. The blocks of FIG. 1 are broken down into greater detail in FIGS. 2A, and 2B and in FIG. 5.

Referring to FIG. 1, the inputs from the patient 61 are first handled in the "Input" block 10, and then fed into two parallel paths, the "QRS Recognition" block 12 and the "Pacing Artefacts Recognition" block 14. The entire circuit is supplied with power and certain safety functions are overlaid, as indicated, from the "Supply and Safety" block 16. Thereafter, the output of the blocks 12 and 14 are fed into the "Logic Processing Output" block 18. The "Surveillance and Alert" block 20 controls the operation of the block 18.

Figure 2A:
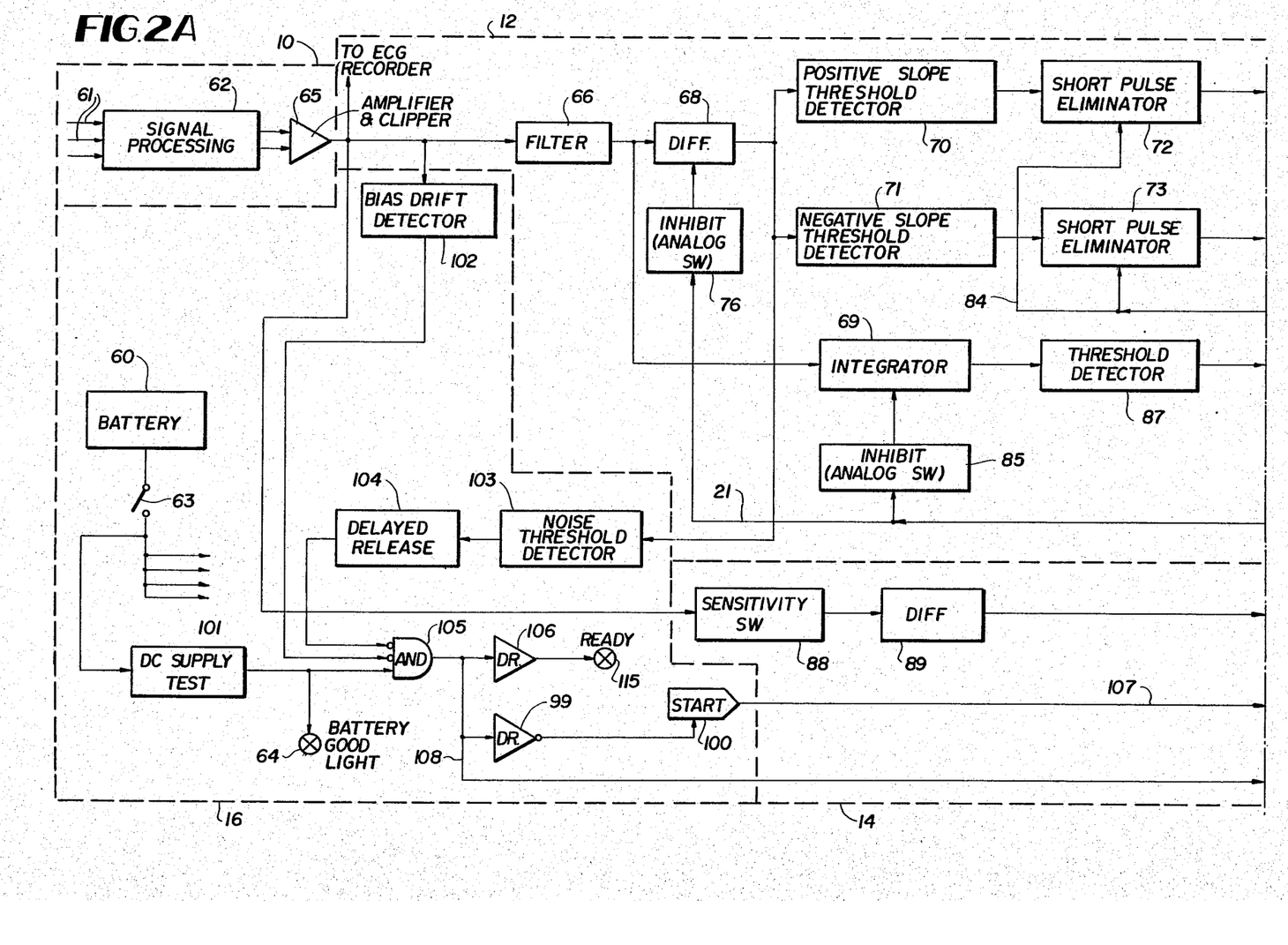
FIGS. 2A and 2B: are block diagrams of most of the invention circuit shown in FIG. 1 concerning input signal processing and auxiliary fail-safe precautions.
Figure 2B:
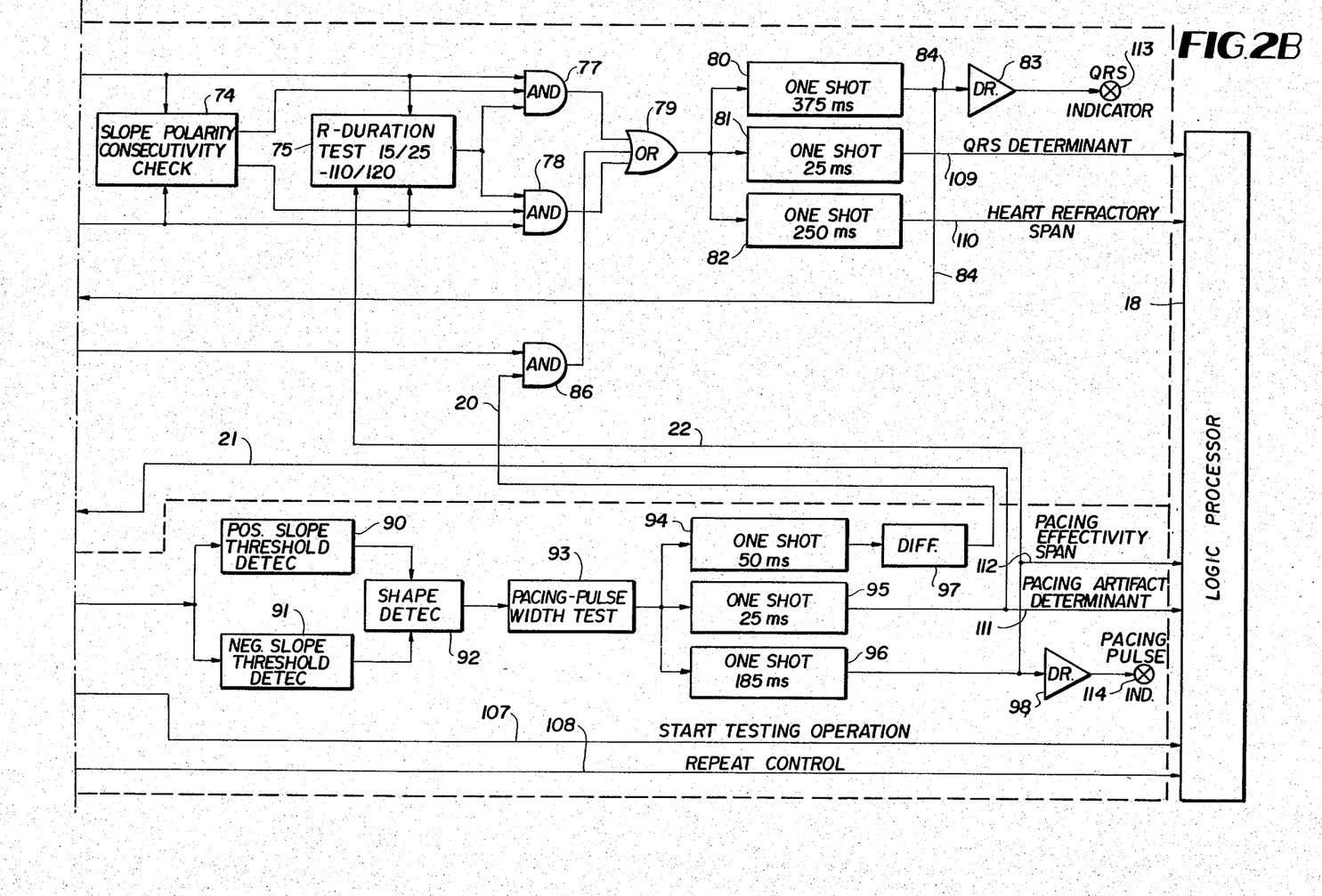

FIGS. 2A and 2B show a block diagram of a part of the preferred embodiment of the PFA. The electrical potentials of the patient being examined are sensed by ECG electrodes 61 connected to the patient in the usual manner, and thence to the instrument embodying the invention and shown overall, in FIG. 1, as circuit 50. The first "Signal Processing" block 62 accomplishes the usual input signal handling processes, including overvoltage protection, impedance conversion, and lead selection. Thereafter, the signals feed into a differential "Amplifier and Clipper 65, which optimizes the signals fed onto the remainder of the circuit. The details of this clipper need not be shown, but is described below.

One principle of the present invention is to allow undistorted processing of QRS-complexes (0.25 to 2.5 mV) in the presence of pacing artefacts (0.3 to 1,000 mV), monitored simultaneously from the patient's body. This is undertaken by clipping the excessive amplitudes of the pacing artefacts at a level at which the QRS still appear undistorted at the output of the clipper 65. Choosing an amplification of 200 and a clipping level at 0.6 volts peak-to-peak, the highest QRS amplitudes of 2.5 mV are amplified to 0.5 volts at the output, which leaves them below the chosen clipping level. This ensures the QRS form to remain unchanged and preserves the information content of the QRS, which is indispensable for providing good accuracy in the further QRS recognition process. As to the pacing artefact, it is in the form of a rectangular pulse, and clipping its amplitude does not influence either the characteristic steepness of the edges or the width of the pulse, which are relevant for its recognition.

Thus, the block 65 operates by taking the relatively small QRS and amplifying it to a level just below the clipping level. The clipping level clips the high unusable parts of the pacing artefacts, thus clarifying the signal which are handled in the succeeding parts of the circuit. This also "cleans up" the signal from extremely strong surges, thus preventing undesirable phenomena such as ringing, overshooting, oscillations, and the like.

Referring now back to FIG. 2A, the "Filter" block 66 segregates out the part of the ECG trace corresponding to the pacing artefact. That signal is handled in the block 14 and described below.

Figure 3:
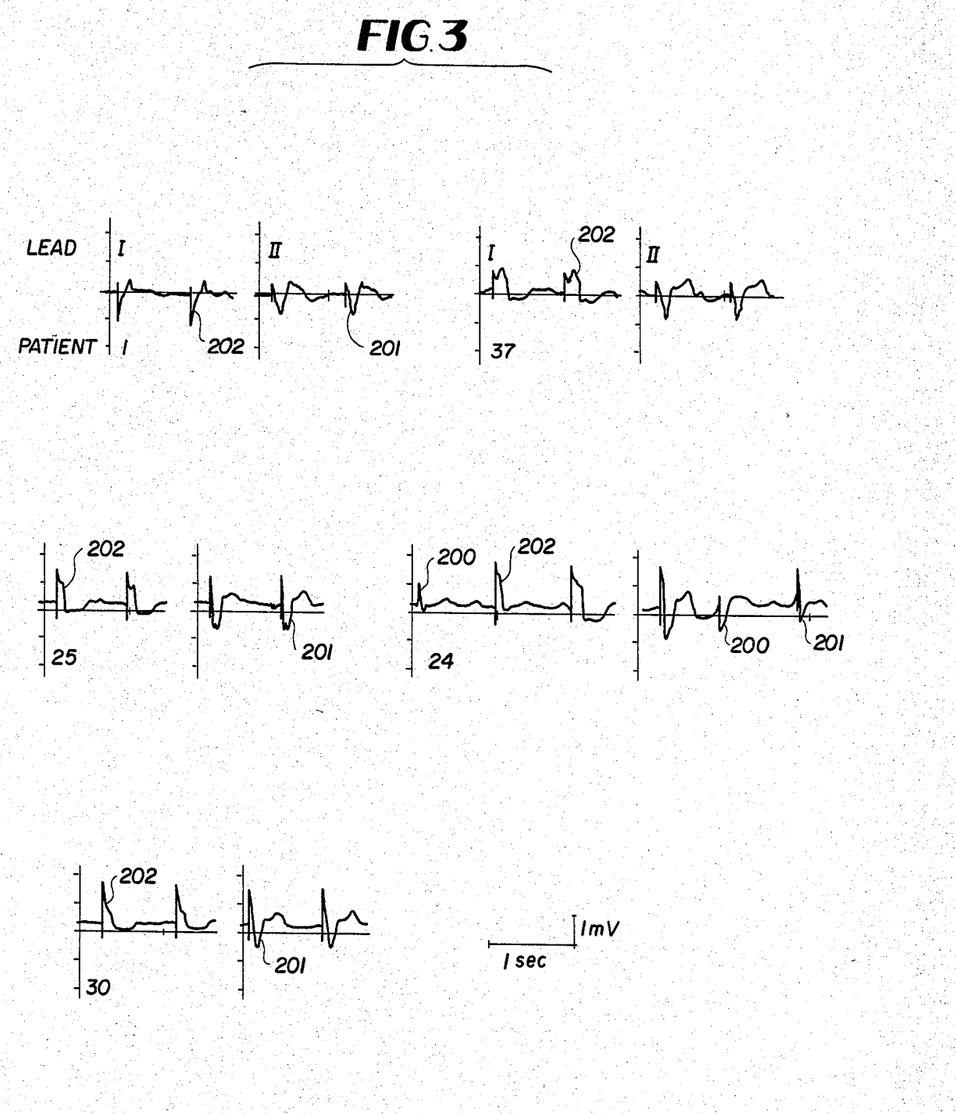
FIG. 3: are typical ECG traces useful in explaining the invention.

FIG. 3 depicts a variety of ECG forms recorded from ECG leads I and II of different patients, when a unipolar endocardial pacemaker electrode is located in the right ventricle at the lower part of the septum (the terminology used here is well known to those skilled in these arts). The examination of the ECGs recorded from the pacemaker patients shows that both spontaneous 200 and paced QRS-complexes, 201 and 202, may be present in the electrogram. Their form depends on the type of the pacemaker electrode (uni-or bi-polar), on its location (endo- or epi-cardial) and on the recorded lead. As is well known to those skilled in these arts, the QRS-complex signal and the pacing artefact can sometimes be separate, as in 201, and can sometimes be fused as in 202, on the ECG traces of FIG. 3. It is an important advantage of the invention that it can operate with both such separate signals and such fused signals, and can do so simultaneously.

To this end, the present invention provides a method and system to recognize spontaneous heartbeats 200 and the paced QRS signal appearing in the form of separated complexes 201. The recognition is executed in the "QRS Recognition" channel 12, and specifically in the "Differentiator" block 68 and in the succeeding portions of the circuitry. This recognition, that is the recognition of the spontaneous and separated complexes, is based on an evaluation of the slew rates or slopes of the QRS signal swings, their direction consecutivity and time durations, all of which is based on extensive empirical observation.

A spontaneous QRS is considered as each signal appearing at the input of the "Amplifier" 65, which initiates with a swing in either direction (positive or negative) and is followed by a swing of opposite polarity; i.e., when the slew rates of both swings amount at least 10 mV/sec, lasting for at least e.g. 9.5 msec; and when the two swings fulfill these conditions, measured at 9.5 msec durations, are parted from each other by a minimum interval of 15 msec and a maximum interval of 110 msec. As a paced separated QRS beat is considered each signal at the input of the "Amplifier" 65 following the occurrence of a pacing artefact by at least 25 msec, which initiates with a swing in either direction (positive or negative) and is followed by a swing of opposite polarity; i.e., when the slew rates of both swings amount at least 10 mV/sec, lasting for at least 9.5 msec; when the two swings fulfilling these conditions, measured at 9.5 msec durations, are parted from each other by a minimum interval of 25 msec and a maximum interval of 120 msec; and when the second swing at 9.5 msec duration comes at a time interval of maximum 185 msec from the occurrence of the pacing artefact.

The blocks 70 and 71 which are fed by the signals from the "Differentiator" 68 determine, respectively, whether the signal has a positive slope or a negative slope, as indicated. The next two blocks 72 and 73 feeding off of blocks 70 and 71, respectively, measure the time duration of the slope portion, which again, referring to the paragraph above, must be at least within the above time limits.

When these cnditions are fulfilled, the output signals from the blocks 72 and 73 are brought in parallel, FIG. 2B, to the blocks 74, 75 and to the first pair of terminals of the gate blocks 77 and 78. Block 74 checks if the two slopes come in the proper sequence, that is negative followed by positive or positive followed by negative. Either sequence assures that we are dealing with a peak. If there was positive followed by positive, this would merely be a change in direction of a line going in one direction. The output of the block 74 is fed onto the second pair of the terminals of the blocks 77 and 78. Block 75 determines whether such peaks are separated by the predetermined time spacing as set forth above. The output of this block is fed to the third terminal pair of the gates 77 and 78. Thus, summarizing this portion of the circuit, the blocks 70 through 74 determine whether or not there is a peak present, while the block 75 determines the width in the time direction of such peaks. When those conditions are fulfilled, that is, there is a peak and it has a duration within the empirically determined values taught by the invention, then one of the "AND" gates 77 and 78 will produce an output fed further into the "OR" gate 79.

The invention also provides means in the "QRS Recognition" block 12 to differentiate between a spontaneous QRS of a patient's heart and paced QRS of the separated form. To this end, FIG. 2A, the "Inhibit (Analog Switch)" block 76 fed by the line 21 from the pacing recognition block 14 provides a time delay of 25 msec to accomodate the time delay between the spike produced by the pacing pulse and the beginning of the QRS signal. Thus, the Differentiator 68 is operated after this 25 msec time lapse, processing only then the information concerning a paced separated QRS-complex, when this is present. Simultaneously, the line 22 from the "Pacing Artefacts Recognition" block 14, FIG. 2B, feeds into the block 75, setting the limits of the separated QRS duration check to be executed by this block.

Thus, an output from the "OR" gate 79 is an indication that there is detected and determined a spontaneous or a paced separated QRS signal from the patient's heart. The output signal of the "OR" gate 79 triggers an array of three "One-Shot" blocks 80, 81 and 82 arranged in parallel and selected to output a time duration signal in the lengths of time indicated on the drawing.

The output of the "One Shot" block 80 is of 375 msec. duration, and this signal is fed back on the line 84 to the blocks 72 and 73. This feedback for this length of time disables the two blocks 72 and 73 to assure that, having detected a proper QRS signal, the circuitry is in effect turned off to allow the passage of the corresponding T (relaxation) wave to pass. After the 375 msec. delay, the circuit at the blocks 72 and 73 is again enabled to permit detection of the next QRS signal. Simultaneously, the ouput of the block 80 drives a "Driver" 83 which lights the "Indicator" light 113 to indicate that there has been a QRS signal detected.

The output of the "One-Shot" block 81 is of 25 msec. duration, and serves as a verification that there has been a QRS signal, which signal is passed on via the line 109 "Logic Processing" block 18 as a QRS determinant marker.

The output of the "One-Shot" block 82 of 250 msec duration simulates the heart refractory span, that is, as is known to those skilled in the medical arts, the period of time during which the heart, which contracted spontaneously or due to an artificial stimulus, does not respond further to a subsequent stimulus, —and it also goes to block 18 via the line 110.

The blocks 69, 85, and 86, and 87, FIGS. 2A and 2B, operate on the other type of QRS signal, namely the so called fused type wherein the QRS signal and the pacemaker artefact are run together on the ECG trace. This recognition of the QRS is based here on integration of the QRS-potential area during a predetermined interval between 25 and 50 msec after the occurrence of a pacing artefact. As a paced fused QRS is considered each signal appearing at the input of the "Amplifier" 65, which shows within the predetermined interval an integrated area of at least 14 mV. msec.

This integration test is accomplished by the "Integrator" 69 and the "Threshold Detector" 87 which cuts off at the predetermined integrated value. The control of the integration period is accomplished by the block 85 fed by a line 21 from the "Pacing Artefacts Recognition" block 14, and by the Gate block 86 fed by a line 20 from block 14. The block 85 is precisely analogous to the block 76 described above, inhibiting the beginning of operation of the "Integrator" 69 for 25 msec.

A predetermined time duration of 50 msec. is provided by signal from the block 14 via the line 20, which feeds one of the inputs of the "AND" gate 86 which also gets the output signal of the "Threshold Detector" 87. The output of the "AND" gate 86 is the third input to the "OR" gate 79 which operates the succeeding portions of the circuitry, as described above.

Referring now to the "Pacing Artefacts Recognition" Circuit 14, FIG. 2A and FIG. 2B, the output of the block 65 is first delivered to the ¢Sensitivity Switch" block 88, a tremor eliminator. In the case where the patient suffers tremors, switching on the block 88, in the nature of a special filter, removes those spurious pulses. The output of block 88 feeds into the "Differentiator" block 89 which differentiates the pacing artefact signal, in a manner analogous to the "Differentiator" 68 in the "QRS Recognition" circuit 12.

Recognition of the pacing artefact signal is based on evaluation of slew rates, or slopes of the edges of the pacing artefact pulse, their direction, consecutivity and parity shape, and the time spacing between them. A pacing artefact is considered, each signal appearing at the input of the Preamplifier 65 initiating with a swing in either direction (positive or negative), followed by a swing of opposite polarity; when the slew rates of both edges amount at least 2.6 V/sec. and are almost equal within a 20% difference and the time interval between them is 0.4 to 3.0 msec. (this interval can be adjusted to the particular type of pacemaker checked). Checking a patient in tremor conditions, the slew rate threshold is heightened to 3.4 V/sec. to avoid mis-recognition of sharp muscular potentials as pacing artefacts.

Blocks 90, 91, 92, and 93, in a manner analogous to the blocks 70, 71, 74, and 75, described above, accomplish these goals. The block 92, when fed by signals of opposite polarity from the blocks 90 and 91 which indicate that we are in fact dealing with a pulse of the proper slopes, determines if the shape of the pulse thus determined by the blocks 90 and 91 is in fact the characteristic shape of a pacing artefact. When all the stated above conditions are fulfilled an output signal at the output of the block 93 is released. Thus, the output at the block 93 is indicative of the occurrence of a proven pacing artefact. This output signal triggers three "One-Shot" blocks 94, 95, and 96, each having a time duration as indicated on the drawing.

The "One-Shot" 94 produces the 50 msec. duration signal which via the "Differentiator" 97 feeds up to the "AND" gate 86 via the line 20 marking the end of the integration time for a fused QRS-complex, as described above.

The 25 msec. output of the "One Shot" 95 feeds as a determinant marker into the "Logic Processor" 18 via the line 111, and serves as a verification that a pacing pulse has occurred. The same signal feeds also via the line 21, the blocks 76 and 85, delaying for 25 msec. the generation of the "Differentiator" 68 and "Integrator" 69, as described above.

The "One Shot" 96 produces a signal of 185 msec. duration which is used, first, via a "Driver" 98 to light a lamp of the "Indicator" 114 to indicate the pacing pulse occurrence. This signal also is delivered to the block 75 in the "QRS Recognition" block 12 via the line 22 for the purpose of indicating that a particular QRS signal detected is in fact a paced separated signal as opposed to being a spontaneous signal. This signal fed up to block 75 determines the time preconditions for the duration of a paced QRS signal handled in the block 12, as described above. Also, the signal from the "One Shot" 96 feeds via the line 112 into the "Logic Process" block 18 to simulate the span of a paced separated QRS for verification of an effective pacing stimulus (the maximum time lapse between the occurrence of a pacing artefact and the moment of recognition of a succeeding QRS).

Still another principle of the present invention is providing fail-safe means to secure the competence of operation of the PFA during pacemaker patient examination. This objective is achieved by constant self-checking of the following operative conditions: (a) the state of the PFA supply battery; (b) the electrogram's (ECG) base-line stability; and (c) the system's noise. These last two conditions serve as an indicator of satisfactory preparation of the electrode-to-body contacts and of lack of spasm of underlying muscle (noise below an experimentally determined threshold), and lack of electrode movements (minute drifts of the bias-line).

To this end, the invention includes a "Battery" 60, a main on-off switch 63, a plurality of lines after the switch which feed into other parts of the circuit as needed, and a "DC Supply Test" circuit 101. A light 64 controlled on by the "Supply Test" 101 indicates that the battery is in working condition. That signal feeds simultaneously into the "AND" terminal of the gate 105 as one of three inputs thereto. The output of the "Differentiator" 68, as explained above, is fed into a "Noise Threshold Detector" 103 and then via a "Delayed Release" 104 as a second input to the "AND" terminal of the gate 105. The third input to the other "AND" terminal of the gate 105 is the output of the "Amplifier" 65 delivered via a "Bias Drift Detector" circuit 102.

When these three conditions are fulfilled, a "Ready" block 115 indicator driven by a "Driver" 106 is lit, and the operator is permitted to begin a test via the line 107 using the manual "Start" button 100. If there is no ready signal, false starting or incorrect starting is automatically prevented by the "Driver" 99 because the "Start" button 100 cannot be activated to pass on a start signal into "Logic Processing" circuitry 18. Further, in the event of failure of one of the three conditions during the running of the test, a signal, via the line 108, will be delivered to the "logic Processing" circuitry 18 to cause the test to stop automatically and indicate the necessity for repeating the test.

The "Bias Drift Detector" circuit 102 checks the electrogram's baseline for undulations higher than the experimentally determined limit of 0.5 mV p-p as related to the input of the "Amplifier" 65. The "Noise-threshold Detector" 103 and the "Delayed Release" 104 circuits provide for evaluation of the noise strength at the output of the "Differentiator" 68 in the "QRS Recognition" channel 12. Basing on experimental results, a measure of an admissible noise threshold was defined as 0.3 mV p-p noise spikes of 100 or 120 Hz (resulting from the most frequent 50 or 60 Hz power lines interferences) lasting for 0.55 sec. The noise spikes are counted in block 103 in the periods between the QRS beats, the counting beginning from the occurrence of the QRS. When the noise during the testing process becomes occasionally higher than the allowed threshold, one of the inputs of the gate 105 becomes deactivated which automatically interrupts the testing procedure, and the necessity of test repetition is signaled. When the appearance of noise is of temporary nature, it takes 1.8 sec. to reactivate the noise controlled input of the gate 105, which permits the repetition of the test. This "fast to operate/slow to release" noise checking arrangement accounts for possible noise fluctuations, to avoid confusion of the operator of the PFA by frequent disruption of the testing procedure.

Figure 5A:
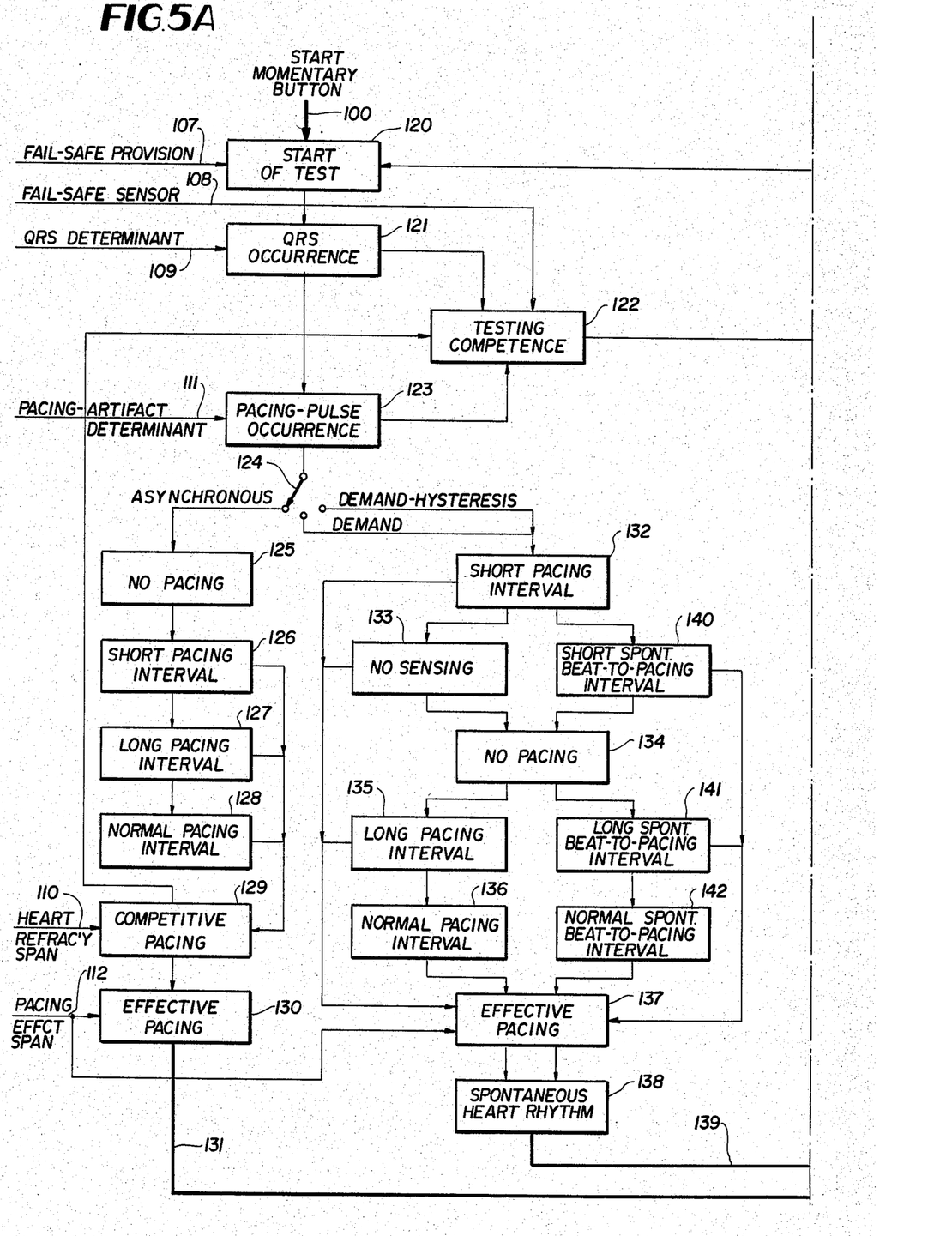
FIGS. 5A and 5B: are a block diagram of the remainder of the circuit shown in FIG. 1 concerning logic processing of determinant signals, display of output conclusions and automatization of long-term surveillance.
Figure 5B:
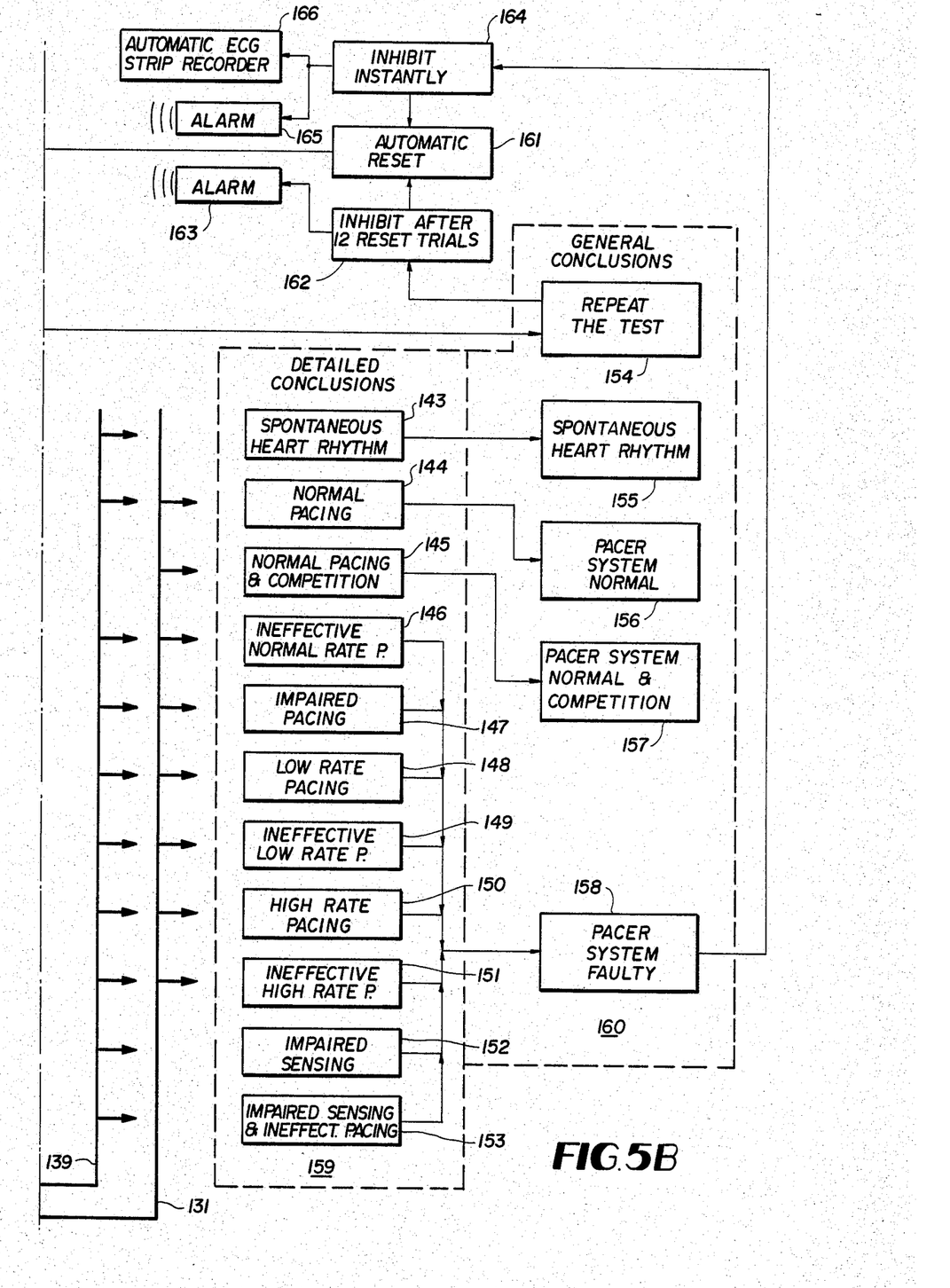

Still another principle of the present invention is in logic processing of the determinant signals designating the occurrence of the QRS - complexes (via line 109) and of the pacing artefacts (via line 111), the heart refractory span (via line 110) and the pacing effectivity span (via line 112), under fail-safe provisions (via line 107 and line 108), as depicted in FIG. 5, for the sake of evaluation of the cardiac pacing function. The information required is delivered to the "Logic Processor" 18, FIG. 2B, from the preceding decoding channels in the form of well-defined rectangular pulses, as described above.

FIGS. 5A and 5B are a block diagram of the remaining parts of the preferred embodiment of FIG. 1. Starting the test of a pacemaker (the analysis of the pacemaker function) is executed by manual operation of a momentary switch which is a part of the circuit of the "Start of Test" block 120. Starting the test becomes allowed under provision that the fail-safe measures installed in the PFA indicate that the pre-conditions for reliable testing are fulfilled, as described above, and that a signal verifying that is sent via the line 107 to the block 120.

The pacemaker testing procedure lasts for the time of occurrence of 8 (eight) heart beats, beginning from the first recognised QRS after operation of the start switch, or for 16 seconds, whichever is shorter. In a case when one of the fail-safe pre-conditions becomes disturbed during the testing procedure, a signal indicating that is fed from the block 105 (FIG. 2A) via the line 108 to the "Testing Competence" block 122, which cancels the proceeding of the test and signals through the "Repeat the Test" block 154 the necessity for repeating the test.

The principles and the succession of the pacemaker testing operations are as follows:

The QRS determinant signals are fed via the line 109 into the "QRS Occurrence" block 121. In a case when a QRS is not being detected for a maximum period of 2,300 msec., or any one of the successive QRS throughout the advance of the testing procedure is not coming at that time interval, the block 121 triggers the block 122, which stops the testing and signalizes the necessity for repeating the test, as described above. The 2,300 msec. period is equivalent to a heart contraction rate of $\sim 26$ beats per minute (b.p.m.), which presents approximately the low heart rate limit in a living person. Non-recognition of a QRS for such a long period, except for a person in a cardiac standstill, may arise occasionally when the monitored ECG lead has not been chosen properly. Namely, when the axis of the heart dipole is nearly perpendicular to the direction of the monitored lead, which results in low amplitude QRS -s. Switching over to another lead improves, normally, the QRS reading. In the case of there being no satisfactory QRS detection in any of the leads (the conclusion "Repeat" appears for all leads), the patient should be directed to a specialized pacemaker clinic for consultation.

The pacing artefact determinant signals are fed via the line 111 to the "Pacing-pulse Occurrence38 block 123. If throughout the advance of the pacemaker testing procedure, one of the (S- to -S) intervals was found to be shorter than the (S- to -S)$_{min}$, equal to the nominal interval adjusted at the pacemaker implantation minus 5% (accounting for a possible inaccuracy of the adjustment, and for varying in environmental conditions), a signal is fed from the block 123 to the block 122, which stops the testing procedure and signals the necessity for repeating the test, as presented above. Such a situation may arise occasionally when a single or two succeeding external signals are induced within the analyser network, imitating the form of pacing pulses. The PFA disregards the occurrence of one such sequence, as this does not allow to draw out a sound conclusion concerning its origin; two such sequences are regarded as a persistent malfunction of the pacemaker, and are treated appropriately as set forth below.

To this point the logic processing is common for testing all pacemaker types including asynchronous, demand and demand-hysteresis pacemakers, and also others which may have a broader application in the future, as e.g. A-V sequential, or atrial-synchronous demand pacemakers. A pacemaker modality switch 124 is operated manually, selecting the logic processing scheme suitable for the analysis of a specific pacemaker type under test.

Testing an asynchronous pacemaker, the primary evaluation concerns its pacing ability which is dealt by the "No Pacing" block 125. When two or more pacing pulses are missing during the testing period (one missing pulse is disregarded by the analyser), this is indicative of a disturbance in pacing. The presence of at least seven pacing pulses serves as evidence of a normal pacing action, as far as it concerns the occurrence of pacing signals. The next question concerns the quality of the rate of pacing. The "Short Pacing Interval" block 126 detects the (S- to -S) intervals which are shorter than the (S- to -S)$_{min}$ interval defined above. The presence of two or more such intervals during the testing period is indicative of high-rate pacing, also known to those skilled in the art as a "running pacemaker". Such a phenomenon may arise as a result of diffusion of the body fluids into the pacemaker's enclosure, which effects shunting of the electronic circuitry components and devices used for determination of the pacing frequency.

The "Long Pacing Interval" block 127 detects the (S- to -S) intervals which are longer than the (S- to -S)$_{max}$ interval, equivalent to the permissible low-rate pacing limit for a given pacemaker. The presence of two or more such intervals (one such interval is disregarded) is indicative of low-rate pacing which results from a discharge of the supply battery of the tested pacemaker below a threshold considered as the limit of the battery's life. The "Normal Pacing Interval" block 128 detects the (S- to -S) intervals which are included between the low and high permissible limits, as described above. Each such interval is indicative of a normal pacing rate. Simultaneously, the pacing pulses are tested for their effectivity in stimulation of the heart contractions. However, for the asynchronous pacer the effectivity test must be preceded by a competition check. This is undertaken by the "Competitive Pacing" block 129 which is fed from the "QRS Recognition" block 12 (FIG. 2B) via the line 110 by a determinant signal simulating the heart retractory period. The check is based on sorting out each pacing pulse which is coming within the heart refractory span and excluding it from the effectivity test. Such a pulse can not be effective in arising a heart contraction by the nature of the heart's response to successive stimulation, as described above. If among the pacing pulses only one is found to be beyond the heart refractory span, this is considered insufficient for drawing out sound conclusions concerning the effectivity of pacing. Then, a signal is fed to the block 122, to signal the necessity of repeating the pacemaker test, as described above. When two or more pulses are coming beyond the heart refractory span, each of them is tested for its effectivity in stimulation of the heart by the "Effective Pacing" block 130. This block is fed through the line 112 with a signal determinant of the pacing effectivity span, and determines whether a recognized paced QRS complex follows the non-competitive pacing pulse within the effectivity span. The pacing pulse is considered then as an effective one. One ineffective pacing pulse is disregarded by the analyser, two or more such pulses lead to a conclusion that the pacing by the tested pacemaker is ineffective.

The conclusions drawn above by the analyser concerning the functioning of an asynchronous pacemaker, are signalled in an integrative form by an array of the "Detailed Conclusions" displays 159. The "Normal Pacing" block 144 states that the pacer-system delivers non-competitive pacing pulses to the heart at a normal rate and that these pulses are effective, causing heart contractions at the rate of pacing. The "Normal Pacing and Competition" block 145 states that, while normal rate effective pacing takes place, also competitive pulses occur throughout the pacing action. Pacing competition by itself is not considered harmful to the patient, but the cardiologist taking care of him should be aware of it (or should be informed by the operator of the test). Competition may be connected with some discomfort to the patient (distressing parasystotes), and with a potential hazard of stimulation during the heart's vulnerable period, a controversial issue of which the pacemaker specialists are aware. The succeeding displays in the blocks 146, 147, 148, 149, 150 and 151 signal various pacemaker system deficiencies detected by the analyser during the test, according to the legends marked on these blocks.

As to various general conclusions concerning the functioning of the tested pacemaker, the detailed conclusions are re-grouped in an array of "General Conclusions" displays 160. It includes the "Repeat the Test" block 156, the "Pacer System-Normal and Competition" block 157, and the "Pacer System-Faulty" block 158. The block legends are self-explanatory. The block 158 comprises information concerning all pacemaker deficiencies, as they are signalled by the blocks 146 to 151.

Testing a demand pacemaker, the first question concerns the quality of the rate of pacing. The "Short Pacing Interval" block 132, detects the (S- to -S) intervals which are shorter than the (S- to -S)$_{min}$ interval specified above for an asynchronous pacemaker. The presence of two or more such intervals during the pacemaker test is indicative of high-rate pacings, as described above. The "No Sensing" block 133 detects the ($R_{spont(spontaneous)}$-to -S) intervals which are shorter than the permissible (S- to -S)$_{min}$ interval defined above (and accounts also for a short delay of ~20 msec in recognition of a spontaneous QRS). The presence of two or more such intervals during the pacemaker test (one interval is disregarded) is indicative of a disturbance in sensing, when the result of checking by the block 132 is negative. The "No Pacing" block 134 detects the cases of ($R_{spont}$ -to-$R_{spont}$) or (S- to -$R_{spont}$) intervals which are longer than the permissible interval (S- to -S)$_{max}$ specified above for an asynchronous pacemaker, and during which intervals no pacing pulses appeared. The absence of pacing pulses during two or more such intervals throughout the pacemaker test (one interval is disregarded) is indicative of a possible disturbance in the pacing action itself or of a low-rate pacing. The "Long Pacing Interval" block 135 detects the (S- to -S) and the ($R_{spont}$ -to -S) intervals which are longer than the permissible (S- to -S)$_{max}$ interval defined above. The presence of two or more such intervals during the pacemaker test (one interval is disregarded) is indicative of low-rate pacing, as described above. Also a combination of two or more ($R_{spont}$ -to-$R_{spont}$), (S- to -$R_{spont}$), ($R_{spont}$-to-S) and (S- to -S) intervals which are longer than the (S- to -S)$_{max}$ defined above, disqualifies the tested pacemaker function as being indicative of low-rate pacing. The "Normal Pacing Interval" block 136 detects the ($R_{spont}$ -to-$R_{spont}$), ($R_{spont}$ -to-S), (S- to -$R_{spont}$) and (S- to -S) intervals which are comprised between the short and the long permissible limits, as presented above for the blocks 132 and 135, respectively. Each such interval is indicative of a normal pacing rate. Simultaneously, all pacing pulses are brought to the "Effective Pacing" block 137 fed via the line 112 with a signal determinant of the pacing effectivity span, to determine whether the pacing is effective, similar to the procedure described above for the block 130 for an asynchronous pacemaker. One ineffective pacing pulse is disregarded by the analyser, two or more such pulses are indicative of ineffective pacing. When no pacing pulses are detected (one is disregarded) throughout the pacemaker testing period, the "Spontaneous Heart Rhythm" block 138 detects whether the ($R_{spont}$ -to -$R_{spont}$) intervals are shorter than the permissible (S- to -S)$_{max}$ interval, defined above. If this is the case, the heart beats spontaneously, and no pacemaker intervention in the form of artificial pacing is required.

The conclusions drawn above by the analyser concerning the functioning of a demand pacemaker, are signalized in an integrative form by the array of the "Detailed Conclusions" displays 159, similar to the display of conclusions for an asynchronous pacemaker, described above. For a demand pacemaker, one of the blocks 143, 144, 146, 147, 148, 149, 150, 151, 152 or 153 is activated signalling the conclusion concerning the functioning of the tested pacemaker system, according to the legend appearing within the respective activated block. General conclusions can be displayed by the "General Conclusions" array 160, as described above for the asynchronous pacemaker.

Testing a demand-hysteresis pacemaker, all the inquiry blocks 132, 133, 134, 135, 136, 137 and 138 are common with the depend pacemaker test, and so are the principles and the sequence of the testing procedures, except the ($R_{spont}$ -to -S) checks which are excluded from the program of the blocks 133, 135 and 136, and the permissible limit in the block 138. The differences in testing these two pacer modalities concern a few points. The "Short Spontaneous Beat-to-Pacing Interval" block 140 detects the ($R_{spont}$ -to -S) intervals which are shorter than the permissible ($R_{spont}$ -to -S)$_{hmin}$ interval specific to a given pacemaker, and equal to the nominal interval minus 5% (accounting for inaccuries in adjustment, for varying enviromental conditions and a delay in QRS recognition by the analyser). These intervals add to those detected in the block 133 and are subjected to the same rules. The block 133 detects whether the ($R_{spont}$ -to -S) intervals are shorter than the permissible ($R_{spont}$ -to -S)$_{hmin}$ interval, as described above; other considerations are the same as for the demand pacemaker. The "Long Spontaneous Beat-to-Pacing Interval" block 141 detects the ($R_{spont}$ -to -S) intervals which are longer than the permissible ($R_{spont}$ -to -S)$_{max}$ intervals, related to the pacemaker supply battery. These intervals add to those detected in the block 135 and are subjected to the same rules. The "Normal Spontaneous Beat-to-Pacing Interval" block 142 detects the ($R_{spont}$ -to -S) intervals which are comprised between the short and long permissible limits, as presented above for the blocks 140 and 141, respectively. These intervals add to those detected in the block 136 and are subjected to the same rules. The block 138 detects whether the ($R_{spont}$ -to -$R_{spont}$) are shorter than the permissible ($R_{spont}$ -to -S)$_{max}$ interval, as defined above; other considerations are the same as for demand pacemaker. As to the "Detailed" and "General Conclusions" display blocks 159 and 160 they are activated, signalling the conclusion concerning the functioning of the tested pacemaker system in the same way as for a demand pacemaker.

In the above description of the logic process, one detected deviation from a normal pacemaker function during the testing procedure is disregarded by the PFA, as it may be due to some unforeseen factor. Two and more events point to a persistent effect. Such a policy has been adopted to lower to a minimum the possibility of false alarms, and thus to avoid unneccessary stresses of the patient and of the caretaking personnel. Looking for intermittent pacing disturbances, it may be advisable to account also a single functional deviation as a failure of the pacemaker system.

Still another principle of the present invention is the arrangement for continuous surveillance of hospitalized pacemaker patients, presented by the "Continuous Surveillance and Alert" block 20 in FIG. 1. It is especially suited for intensive care of this particular group of patients. Automatic means are provided for continuous sequential resetting of the testing process by the PFA, to call attention of the care-taking medical staff in case of prolonged electrode faults and to alert the staff in case of a pacing failure. The PFA can be easily interfaced with a conventional Coronary Care Unit joining the existing signalling capacities of such a system, including automatic ECG recording in case of a pacing failure; or self-contained alert facilities and an ECG strip recorder can be integrated within the PFA system. The potential utility of the automatic surveillance of patients concerns also the possibility of detection and diagnosis of intermittent pacing failures which may be difficult to expose otherwise, when for practical reasons only a short lasting test of the pacemaker patient by the attending physician is possible.

To this end, FIGS. 5A and 5B show a block diagram of another part of the preferred embodiment of the PFA, presenting the arrangement for continuous surveillance of pacemaker patients. The "Automatic Reset" block 161 feeds a signal into the block 120, which after a short time (e.g. 1 to 2 seconds) after every completion of a pacemaker testing run by the analyser, automatically resets a new subsequent pacemaker test; provided, there is no indication of a pacemaker failure. After completion of each testing run, the display blocks 159 and 160 display the relevant conclusion and this stays on, until it is changed by a different conclusion coming as a result of a subsequent testing run. In case of a conclusion to repeat the test signalled by the block 154, which is due to the failure to meet any of the failsafe precautions, the automatic reset of the testing takes place, continuing for 12 trials as long as the "repeat" conclusion continues to stay on. After 12 unsuccessful trials to resume the test, the "Inhibit After 12 Reset Trials" block 162 feeds a signal into the block 161 stopping the automatic reset of the testing; simultaneously, another signal fed into the "Alarm" block 163 triggers an alarm to alert the personnel taking care of the patient. This is especially useful in cases of intermittent disorders in the electrodes-to-body contacts, which is a common occurrence in the intensive care units, causing false alarms and unneccesary concern to the personnel. The arrangement presented here prevents the drawback to a large extent. In the case of a short-lasting electrode fault, the PFA resumes testing anew automatically after the disturbance ceased by itself, without calling in the medical staff. When the disturbance prolongs, the PFA tries to resume testing 12 times successively, and only then it signals the occurrence of the fault. In the case that a pacemaker failure is being detected, the "Inhibit Instantly" block 164 feeds signal into the block 161, stopping the automatic reset of the testing. Simultaneously, another signal fed into the block 165 triggers an alarm to alert the personnel taking care of the patient; still another signal is fed into the "Automatic ECG Strip Recorder" block 166 which starts automatically an ECG recorder and releases a strip containing the ECG record during the period when the failure event occured.

Figure 4:
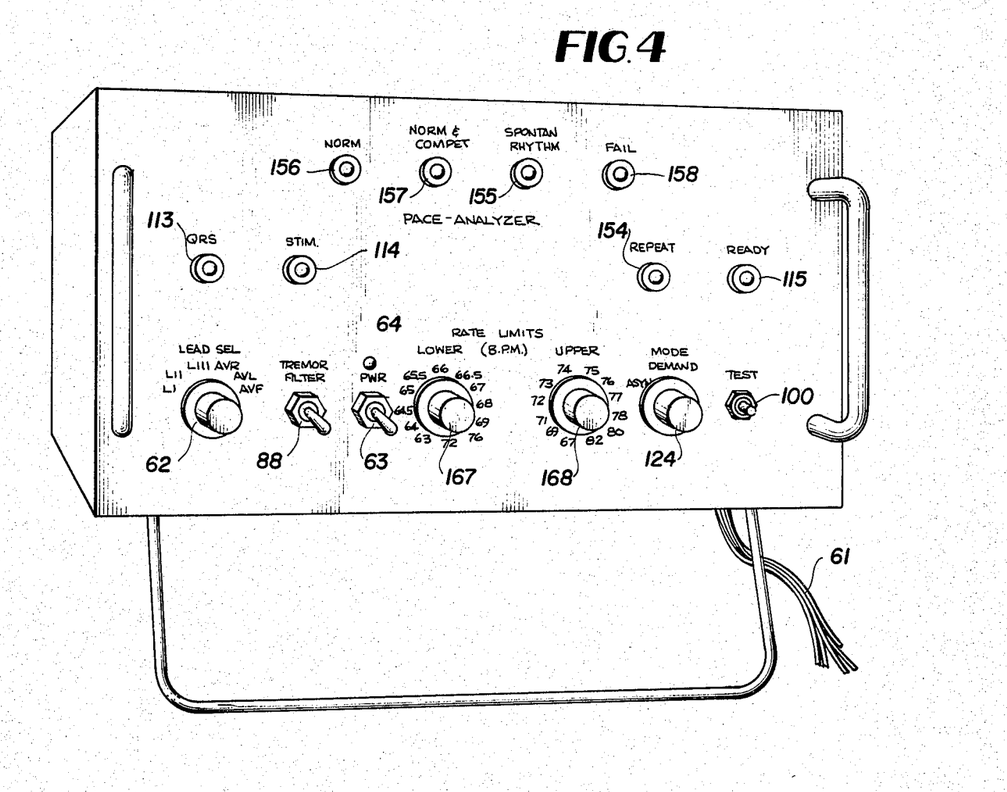
FIG. 4: is a front elevational view of a successfully constructed embodiment of the invention.

FIG. 4 shows the front panel of a PFA prototype used in the last development stages of the analyser and applied successively in clinical studies of pacemaker patients. The solution used here for operation of the PFA and for handling the pacemaker patients, may serve as a model for other types of PFA instruments using different construction and techniques to achieve the goal of reliable testing of the pacemaker function. The legends are largely self-explanatory.

The operator using the switch 124 selects, before beginning the test, the sort of logic processing in accordance to the type of the implanted pacemaker to be tested (asynchronous, demand, demand-hysteresis). Using the high-rate limit selector 168 and the low-rate limit selector 167, he adjusts the permissible limits suitable to the particular pacemaker to be tested, as described above. Then, the attaches the electrodes 61 to the patients limbs, according to the conventional procedures used for ECG recording; care should be taken to ensure a good and steady electrical contact between the electrodes and the underlying skin. Turning on the main on-off switch 63, the electrical supply is delivered to all parts of the instrument; the light 64 signals that the switch 63 is on and verifies that the analyser's battery, which is periodically rechargeable, remains in working condition (the voltage of the battery loaded by the PFA circuitry is above a determined depletion threshold). Using the ECG lead selector 62, the operator selects the optimal lead for monitoring by the analyser. Monitoring is considered satisfactory when the QRS indicator light 113 blinks periodically according to the patient's heart beat, which can be checked e.g. by palpation of his peripheral pulse. The pacing pulse indicator light 114 signalized simultaneously the occurence of the pacing artefacts (they should come periodically for an asynchronous pacemaker; they can come periodically, be intermittent, or be completely absent for a demand pacemaker). When the determined fail-safe preconditions are fulfilled, the "Ready" light 115 is lit, which indicates that the PFA is ready to carry out a reliable test. Pushing the start button 100 initiates the testing procedure. If during the test the Logic Processor 18 does not receive sufficient information to carry out a dependable analysis, or any of the fail-safe precautions controlling the gate 105 becomes disturbed, the testing procedure stops and the conclusion display 154 signals the necessity for repeating the test. When not impeded, the testing procedure becomes completed during 8 heart beats or during 16 seconds, whichever is shorter. One of the conclusion displays 156, 157, 155 or 158 is turned on, indicating: (a) a normally functioning pacing system—display 156, (b) a normally functioning system accompanied by competitive pacing-display 157 (in case of an asynchronous pacer), (c) a spontaneous rhythm-display 155 (in case of a demand pacer), or (d) a failure in the pacing system—display 158.

While the invention has been described in detail above, it is to be understood that this detailed description is by way of example only, and the protection granted is to be limited only within the spirit of the invention and the scope of the following claims.

I claim:

1. A method for automatically evaluating the quality of the performance of a cardiac pacing system including a human heart and an electronic pacemaker, said method operating in a beat-to-beat on-line manner, comprising the steps of:

continuously sensing the electrical pontentials appearing on the body surface of the human whose heart is part of the cardiac pacing system;

determining the presence of a pacing artifact in said electrical potentials by analyzing for the presence of an artifact peak and comparing said peak's shape to the known shape of an artifact signal;

marking the appearance of each said pacing artifact by generating a pacing artifact determinant pulse signal defined in time and duration;

determining the presence in said electrical potentials of a QRS signal of either a spontaneous, paced separate or paced fused nature, including the steps of determining for the presence of a peak, comparing said peaks's shape to the known shape of a spontaneous or paced separate QRS peak, analyzing the time interval between the QRS peak and the occurrence of the previous pacing artifact, and analyzing the integral of the electrical potentials throughout a predetermined time interval after the occurrence of a pacing artifact;

marking the appearance of each said QRS signal by generating a QRS determinant pulse signal defined in time and duration; and evaluating the interrelation between the heart and the pacemaker and the quality of the pacemaker function by analyzing the interrelationship of said pacing artifact and QRS determinant pulses.

2. A method of accordance with claim 1, further including the steps of:

allowing analog, interference-free and noise-free processing of QRS signals of 0.25 to 2.5 mV in the presence of pacing artifact signals of 0.3 to 1,000 mV by amplifying both said QRS and pacing artifact signals by a gain of about 200 to a level of 50 to 500 mV for QRS and about 60 mV to 200 V for pacing artifacts; and clipping said pacing artifact signals at a level of about 600 mV to preserve the information contained in both said QRS and said pacing artifact signals, whereby undesirable effects in the electronic circuitry such as ringing, overshooting, oscillations and the like, which may be caused by high amplitude pacing artifact signals, are prevented.

3. A method in accordance with claim 1, wherein said step of determining the presence of a QRS signal includes analysing for the presence of a spontaneous QRS signal by determining the presence of a peak with consecutive rising and falling (or vice-versa) slopes of at least 10 mV/sec, each slope lasting for at least 9.5 msec, with the marked 9.5 msec ends of the slopes being parted from each other by a minimum of 15 msec and a maximum of 110 msec.

4. A method in accordance with claim 1, wherein said step of determining the presence of a QRS signal includes analyzing for the presence of a paced separate QRS signal by determining the presence of a peak with consecutive rising and falling (or vice-versa) slopes of at least 10 mV/sec, each slope lasting for at least 9.5 msec, with the marked 9.5 msec ends of the slopes being parted from each other by a minimum of 25 msec and a maximum of 120 msec, the beginning of the QRS signal following a pacing artifact by a minimum of 25 msec and a maximum of 185 msec.

5. A method in accordance with claim 1, wherein said step of determining the presence of a QRS signal includes analysing for the presence of a paced fused QRS signal by determining whether the integral of the electrical potential throughout a time interval between 25 and 50 msec after the occurrence of a pacing artifact, equals at least 14 mV msec.

6. A method in accordance with claim 1, wherein said step of determining the presence of a pacing artifact comprises determining whether the human is in tremor conditions, and determining the presence of a peak with consecutive rising and falling (or vice-versa) slopes of at least 2.6 V/sec, or 3.4 V/sec for a human in tremor conditions, the slopes being equal to each other within a difference of 20%, with the distance between the leading and trailing edges being between 0.4 msec and the nominal pacing pulse width of the particular pacemaker.

7. A method in accordance with claim 1, further including the steps of generating auxiliary signals simulating predetermined features of heart behavior including heart refractory span and pacing effectivity span, and wherein said evaluating step includes analysis of the interrelationship of all of said pacing artifact determinant pulses, QRS determinant pulses, heart refractory span signals and pacing effectivity span signals.

8. A method in accordance with claim 7, wherein said heart refractory span signal is generated 250 msec following a QRS signal and said pacing effectivity span signal is generated 185 msec following a pacing artifact signal.

9. A method in accordance with claim 1, wherein said sensing step is accomplished by means of an electrocardiograph, including electrode-to-body contacts, and wherein the method is accomplished by apparatus which includes a battery, and further including the step of constant self-checking of conditions serving as indicators of the state of the battery, satisfactory preparation of the electrode-to-body contacts and lack of spasm of underlying muscle, and lack of electrode movements, and providing an output when said conditions are unsatisfactory.

10. A method in accordance with claim 9, wherein said self-checking step includes determining whether the battery output voltage is below a predetermined lowest acceptable voltage, determining whether the noise is below an experimentally determined threshold, and determining whether the ECG biasline drifts beyond a predetermined amount.

11. A method in accordance with claim 9, wherein said evaluating step includes indicating a failure of the cardiac pacing system, and further including the steps of automatically signalling when said unsatisfactory condition output continues for a predetermined time, and instantly alarming in the event that said evaluating step determines that failure of the cardiac pacing system has occurred.

12. An apparatus for automatically evaluating the quality of the performance of a cardiac pacing system including a human heart and an electronic pacemaker, said apparatus operating in a beat-to-beat on-line manner, comprising:
   means for continuously sensing the electrical potentials appearing on the body surface of the human whose heart is part of the cardiac pacing system;
   means for determining the presence of a pacing artifact in said electrical potentials by analyzing for the presence of an artifact peak and comparing said peak's shape to the known shape of an artifact signal;
   means for marking the appearance of each said pacing artifact by generating a pacing artifact determinant pulse signal defined in time and duration;
   means for determining the presence in said electrical potentials of a QRS signal of either a spontaneous, paced separate or paced fused nature, including means for determining for the presence of a peak, means for comparing said peak's shape to the known shape of a spontaneous or paced separate QRS peak, means for analyzing the time interval between the QRS peak and the occurrence of the previous pacing artifact, and means for analyzing the integral of the electrial potential throughout a predetermined time interval after the occurrence of a pacing artifact;
   means for marking the appearance of each said QRS signal by generating a QRS determinant pulse signal defined in time and duration; and
   means for evaluating the interrelation between the heart and the pacemaker and the quality of the pacemaker function by analyzing the interrelationship of said pacing artifact and QRS determinant pulses.

13. An apparatus in accordance with claim 12, further including:
   means for allowing analog, interference-free and noise-free processing of QRS signals of 0.25 to 2.5 mV in the presence of pacing artifact signals of 0.3 to 1,000 mV by amplifying both said QRS and pacing artifact signals by a gain of about 200 to a level of 50 to 500 mV for QRS and about 60 mV to 200 V for pacing artifacts; and
   means for clipping said pacing artifact signals at a level of about 600 mV to preserve the information contained in both said QRS and said pacing artifact signals,
   whereby undesirable effects in the electronic circuitry such as ringing, overshooting, oscillations and the like, which may be caused by high amplitude pacing artifact signals, are prevented.

14. An apparatus in accordance with claim 12, wherein said means for determining the presence of a QRS signal includes means for analysing for the presence of a spontaneous QRS signal by determining the presence of a peak with consecutive rising and falling (or vice-versa) slopes of at least 10 mV/sec, each slope lasting for at least 9.5 msec, with the marked 9.5 msec ends of the slopes being parted from each other by a minimum of 15 msec and a maximum of 110 msec.

15. An apparatus in accordance with claim 12, wherein said means for determining the presence of a QRS signal includes means for analysing for the presence of a paced separate QRS signal by determining the presence of a peak with consecutive rising and falling (or vice-versa) slopes of at least 10 mV/sec, each slope lasting for at least 9.5 msec, with the marked 9.5 msec ends of the slopes being parted from each other by a minimum of 25 msec and a maximum of 120 msec, the beginning of the QRS signal following a pacing artifact by a minimum of 25 msec and a maximum of 185 msec.

16. An apparatus in accordance with claim 12, wherein said means for determining the presence of a QRS signal includes means for analysing for the presence of a paced fused QRS signal by determining whether the integral of the electrical potential throughout a time interval between 25 and 50 msec after the occurrence of a pacing artifact, equals at least 14 mV msec.

17. An apparatus in accordance with claim 12, wherein said means for determining the presence of a pacing artifact comprises means for determining whether the human is in tremor conditions, and means for determining the presence of a peak with consecutive rising and falling (or vice-versa) slopes of at least 2.6 V/sec, or 3.4 V/sec for a human in tremor conditions, the slopes being equal to each other within a difference of 20%, with the distance between the leading and trailing edges being between 0.4 msec and the nominal pacing pulse width of the particular pacemaker.

18. An apparatus in accordance with claim 12, further including means for generating auxiliary signals simulating predetermined features of heart behavior including heart refractory span and pacing effectivity span, and wherein said means for evaluating the interrelationship between the heart and the pacemaker includes means for analysis of the interrelationship of all of said pacing artifact determinant pulses, QRS determinant pulses, heart refractory span signals and pacing effectivity span signals.

19. An apparatus in accordance with claim 18, wherein said means for generating auxiliary signals causes a heart refractory span signal to be generated 250 msec following a QRS signal and causes a pacing effectivity span signal to be generated 185 msec following a pacing artifact signal.

20. An apparatus in accordance with claim 12, wherein said means for sensing comprises an electrocardiograph, including electrode-to-body contacts, and further including a battery for driving the various means, means for constant self-checking of conditions serving as indicators of the state of the battery, satisfactory, preparation of the electrode-to-body contacts and lack of spasm of underlying muscle, and lack of electrode movements, and means for providing an output when said conditions are unsatisfactory.

21. An apparatus in accordance with claim 20, wherein said means for self-checking includes means for determining whether the battery output voltage is below a predetermined lowest acceptable voltage, means for determining whether the noise is below an experimentally determined threshold, and means for determining whether the ECG bias-line drifts beyond a predetermined amount.

22. An apparatus in accordance with claim 20, wherein said means for evaluating the interrelation between the heart and the pacemaker includes means for indicating a failure of the cardiac pacing system, and further including means for automatically signalling when said unsatisfactory condition output continues for a predetermined time, and means for instantly alarming in the even that said evaluating means determines that failure of the cardiac pacing system has occurred.

* * * * *